(12) United States Patent
Morishima

(10) Patent No.: US 9,978,358 B2
(45) Date of Patent: May 22, 2018

(54) SOUND GENERATOR DEVICE AND SOUND GENERATION METHOD

(71) Applicant: Yamaha Corporation, Hamamatsu-shi, Shizuoka-Ken (JP)

(72) Inventor: Morito Morishima, Fukuroi (JP)

(73) Assignee: Yamaha Corporation, Hamamatsu-shi (JP)

( * ) Notice: Subject to any disclaimer, the term of this patent is extended or adjusted under 35 U.S.C. 154(b) by 598 days.

(21) Appl. No.: 14/284,849

(22) Filed: May 22, 2014

(65) Prior Publication Data

US 2014/0350706 A1     Nov. 27, 2014

(30) Foreign Application Priority Data

May 23, 2013  (JP) .................................. 2013-108820

(51) Int. Cl.
*G06F 17/00*     (2006.01)
*G10K 15/04*     (2006.01)
(Continued)

(52) U.S. Cl.
CPC ............ *G10K 15/04* (2013.01); *A61B 5/0482* (2013.01); *A61B 5/4812* (2013.01);
(Continued)

(58) Field of Classification Search
CPC ... A61B 5/0482; A61B 5/4812; A61B 5/4815; A61M 21/02; A61M 2021/0033;
(Continued)

(56) References Cited

U.S. PATENT DOCUMENTS 5,036,858 A     8/1991   Carter et al.
5,267,942 A *  12/1993   Saperston .......... A63B 71/0686
                                                    128/905
(Continued)

FOREIGN PATENT DOCUMENTS

EP     2 537 550 A1     12/2012
JP     4-269972 A        9/1992
(Continued)

OTHER PUBLICATIONS

Japanese Office Action issued in counterpart Japanese Application No. 2013-108820 dated May 17, 2016, with English translation (three (3) pages).

(Continued)

*Primary Examiner* — Hemant Patel
(74) *Attorney, Agent, or Firm* — Crowell & Moring LLP

(57) ABSTRACT

A sound generator device includes an acquisition unit configured to acquire biological information on a subject user, an estimation unit configured to estimate, based on the biological information, a mind and body state relating to sleep of the subject user. The sound generator also includes a sound generator configured to output a sound signal based on a plurality of control patterns stored in advance and a sound generator control unit configured to select, based on the estimated mind and body state, at least one control pattern among the plurality of control patterns. The sound generator outputs the sound signal based on the at least one control pattern.

6 Claims, 9 Drawing Sheets

(51) Int. Cl.
*A61B 5/0482* (2006.01)
*A61M 21/02* (2006.01)
*A61B 5/00* (2006.01)
*A61M 21/00* (2006.01)

(52) U.S. Cl.
CPC .......... *A61B 5/4815* (2013.01); *A61M 21/02* (2013.01); *A61M 2021/0033* (2013.01); *A61M 2021/0038* (2013.01); *A61M 2230/06* (2013.01); *A61M 2230/30* (2013.01); *A61M 2230/42* (2013.01); *A61M 2230/50* (2013.01); *A61M 2230/63* (2013.01)

(58) Field of Classification Search
CPC ...... A61M 2021/0038; A61M 2230/06; A61M 2230/30; A61M 2230/42; A61M 2230/50; A61M 2230/63; G10K 15/04
USPC .......................................... 379/37–52; 700/94
See application file for complete search history.

(56) References Cited

U.S. PATENT DOCUMENTS

| | | | |
|---|---|---|---|
| 6,206,821 | B1 | 3/2001 | Rhee |
| 2004/0143193 | A1* | 7/2004 | Nissila ................. A61B 5/024 600/519 |
| 2005/0120976 | A1 | 6/2005 | Kim et al. |
| 2007/0083079 | A1 | 4/2007 | Lee et al. |
| 2007/0084473 | A1 | 4/2007 | Hewett |
| 2009/0149699 | A1 | 6/2009 | Ullmann |
| 2010/0048985 | A1 | 2/2010 | Henke et al. |
| 2010/0125218 | A1 | 5/2010 | Haartsen et al. |
| 2011/0245633 | A1* | 10/2011 | Goldberg ............... A61B 5/681 600/301 |
| 2012/0295589 | A1* | 11/2012 | Alexander .......... H04L 63/0861 455/411 |
| 2014/0307878 | A1* | 10/2014 | Osborne ........... G06F 17/30743 381/56 |
| 2015/0038776 | A1 | 2/2015 | Donnet et al. |

FOREIGN PATENT DOCUMENTS

| | | |
|---|---|---|
| JP | 6-35490 A | 2/1994 |
| JP | 9-187512 A | 7/1997 |
| JP | 2001-224690 A | 8/2001 |
| JP | 2004-344284 A | 12/2004 |
| JP | 2005-040440 A | 2/2005 |
| JP | 2005-87572 A | 4/2005 |
| JP | 2007-98138 A | 4/2007 |
| JP | 2008-525055 A | 7/2008 |
| JP | 2009-172371 A | 8/2009 |
| JP | 2009-195450 A | 9/2009 |
| JP | 2009-284998 A | 12/2009 |
| JP | 2010-82377 A | 4/2010 |
| JP | 2011-255008 A | 12/2011 |
| WO | WO 2008/009978 A1 | 1/2008 |
| WO | WO 2008/148433 A1 | 12/2008 |
| WO | WO 2012/175704 A1 | 12/2012 |

OTHER PUBLICATIONS

European Search Report dated Aug. 21, 2014 and European Search Opinion (Ten (10) pages).
Japanese-language Office Action issued in counterpart Japanese Application No. 2017-054276 dated Jan. 30, 2018 with English translation (five (5) pages).
Japanese-language Office Action issued in counterpart Japanese Application No. 2017-054277 dated Feb. 6, 2018 with English translation (five (5) pages).
Japanese-language Office Action issued in counterpart Japanese Application No. 2017-054278 dated Feb. 6, 2018 with English translation (four (4) pages).

* cited by examiner

FIG.3

<CONTROL TABLE>

| CONTROL MODE | CONTROL PATTERN |||||||||||
|---|---|---|---|---|---|---|---|---|---|---|
| | HYPERSONIC (410) | BINAURAL BEAT (420) | NATURAL SOUND (430) |||| MUSIC (440) ||||
| | | | 1/f | TEMPO CONTROL | BEAT CONTROL | VOLUME | 1/f | TEMPO CONTROL | BEAT CONTROL | VOLUME |
| RELAXATION | ○ | ○ DIFFERENCE 7~14Hz | × | × | × | × | ○ | ○ -3 | ○ 4 | MEDIUM |
| SLEEP ONSET | ○ | ○ DIFFERENCE 4~7Hz | ○ | ○ -3 | ○ 4 | SMALL | × | × | × | × |
| GOOD SLEEP | ○ | × | ○ | ○ -2 | ○ 4 | SMALL | × | × | × | × |
| AMBIENT | ○ | × | × | × | × | × | × | × | × | × |
| WAKE-UP | × | × | × | × | × | × | × | ○ TWICE | ○ 2 | LARGE |
| MUTE | × | × | × | × | × | × | × | × | × | × |

SOUND GENERATOR DEVICE AND SOUND GENERATION METHOD

CROSS-REFERENCE TO RELATED APPLICATION

The present application claims priority from Japanese application JP 2013-108820 filed on May 23, 2013, the content of which is hereby incorporated by reference into this application.

BACKGROUND OF THE INVENTION

1. Field of the Invention

The present invention relates to a sound generator device and a sound generation method.

2. Description of the Related Art

In recent years, there has been proposed a technology for improving sleep and imparting relaxation effects by detecting biological information such as a body motion, breathing, and heartbeat and generating a sound in accordance with the biological information (see, for example, Japanese Patent Application Laid-open No. Hei 04-269972). There has also been proposed a technology for adjusting at least one of the kind, volume, or tempo of a sound to be generated in accordance with the relaxed state of a subject user (see, for example, Japanese Patent Application Laid-open No. 2004-344284).

SUMMARY OF THE INVENTION

By the way, it has been pointed out that, in the case of improving sleep or the like by the generation of a sound, when the sound is monotonous, the sound rather hinders sleep or the like for the reason that the sound is boring and annoying. One or more embodiments of the present invention has been made in view of the above-mentioned circumstance, and one object of one or more embodiments of the present invention is to provide a sound generator device and a sound outputting method which are designed so as not to give a boring feeling, an annoying feeling, or the like to a subject user, in the case of improving sleep or the like with a sound to be generated.

In one or more embodiments of the present invention, a sound generator device includes an acquisition unit configured to acquire biological information on a subject use and an estimation unit configured to estimate, based on the biological information, a mind and body state relating to sleep of the subject user. The sound generator device also includes a sound generator configured to output a sound signal based on a plurality of control patterns stored in advance and a sound generator control unit configured to select, based on the estimated mind and body state, at least one control pattern among the plurality of control patterns. The sound generator outputs the sound signal based on the at least one control pattern.

In one or more embodiments of the present invention, a sound generation method includes acquiring biological information on a subject user, estimating, based on the biological information, a mind and body state relating to sleep of the subject user. The sound signal outputting method also includes selecting, based on the estimated mind and body state, at least one control pattern among a plurality of control patterns stored in advance and outputting a sound signal based on the at least one control pattern.

In one or more embodiments of the present invention, a sound generator device, includes an acquisition unit configured to acquire biological information on a subject and a plurality of sound generator units each configured to output a sound signal. The plurality of sound generator units include at least a first sound generator unit and a second sound generator unit. The first sound generator unit outputs the sound signal at a tempo in accordance with the biological information acquired in the acquisition unit. At least one of the first sound generator unit or the second source unit includes a reading unit configured to read waveform data indicating a sound waveform from a waveform memory. The reading unit sets a section that has a range from starting a reading to finishing a reading of the waveform data in a predetermined rule or at random. The reading unit reads the waveform data in the set section, and outputs a sound signal based on the read waveform data.

According to one or more embodiments of the present invention, the sound signal output from the first sound generator unit has a tempo in accordance with the biological information so as to improve a subject user's sleep. Further, at least one of the first sound generator unit or the second sound generator unit outputs the sound signal based on the waveform data read from the waveform memory, and the waveform data read at this time is almost at random so as not to be predicted by the subject. Therefore, the sound signal does not give a boring feeling or an annoying feeling to the subject. Note that, in one or more embodiments of the present invention, the plurality of sound generator units simultaneously output different sounds in some cases, which are not recognized as music but changes the mind and body state of the subject user.

In one or more embodiments of the present invention, the plurality of sound generator units may include a third sound generator unit. The third sound generator unit may include a first reproduction unit configured to output a first signal obtained by reproducing the waveform data stored in the waveform memory at a predetermined speed, a second reproduction unit configured to output a second signal obtained by reproducing the waveform data at a speed higher than the predetermined speed, and a mixing unit configured to mix the first signal with the second signal and to output the mixed signal as the sound signal.

This configuration generates a mixture of an audible sound obtained by reproducing the waveform data at a predetermined speed and an inaudible sound obtained by reproducing the waveform data at a higher speed so that healing effects ascribed to hypersonic effects are expected.

In one or more embodiments of the present invention, the sound generator device may further include an estimation unit configured to estimate a mind and body state of the subject from the acquired biological information on the subject user and a sound generator control unit configured to control the plurality of sound generator units in accordance with the estimated mind and body state. Accordingly, it is realized that the plurality of sound generator units are controlled in accordance with the estimated mind and body state of the subject.

Further, in one or more embodiments of the present invention, it is preferred that at least one of the plurality of sound generator units impart fluctuation to one of an amplitude and a pitch of a sound signal to be output. By imparting the fluctuation to the one of the amplitude and the pitch as described above, the sound signal is prevented from being boring or annoying. Note that, the degree of the fluctuation may be defined in accordance with the acquired biological information.

Note that, one or more embodiments of the present invention may be realized not only as the sound generator device but also as a program for controlling a computer to function as the sound generator device. Also, one or more embodiments of the present invention may be realized as a sound outputting method.

BRIEF DESCRIPTION OF THE DRAWINGS

FIG. 3 is a diagram showing an example of a control table in a sound generator control unit of the sound generator device.

DETAILED DESCRIPTION OF THE INVENTION

Now, an embodiment of the present invention is described with reference to the drawings.

Figure 1:
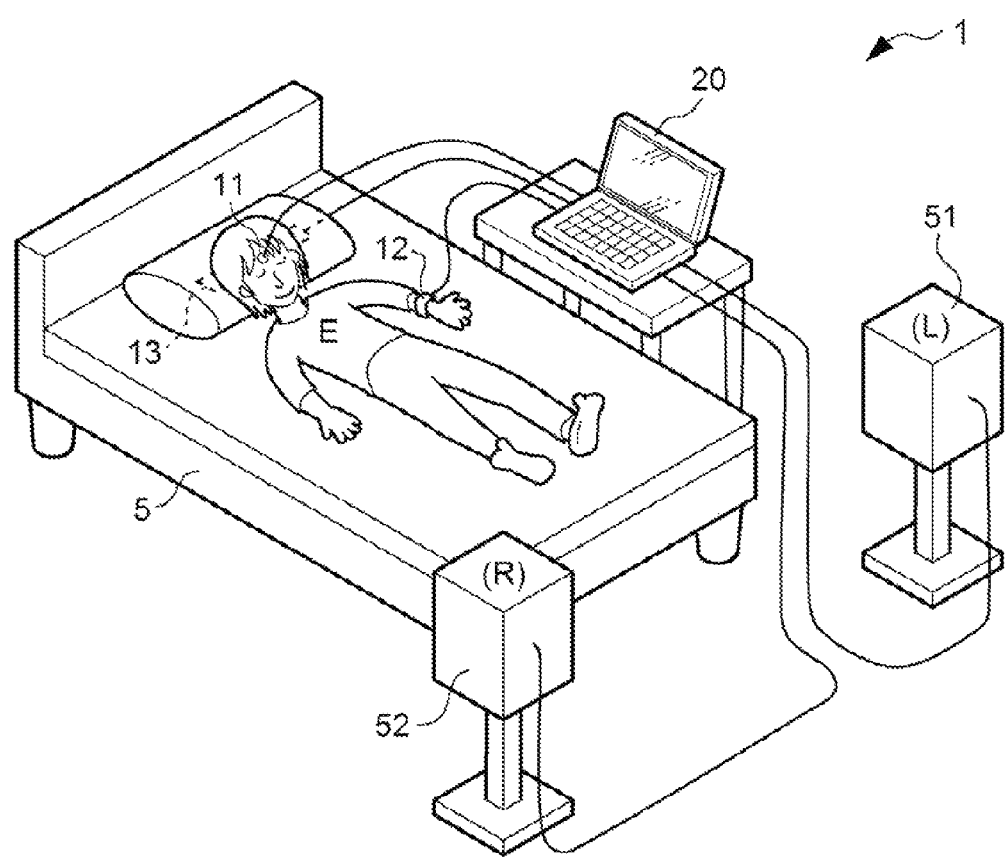
FIG. 1 is a view illustrating an entire configuration of a system including a sound generator device according to an embodiment of the present invention.

FIG. 1 is a view illustrating an entire configuration of a system 1 including a sound generator device 20 according to the embodiment of the present invention. As illustrated in FIG. 1, the system 1 includes sensors 11, 12, 13, the sound generator device 20, and loudspeakers 51, 52. The system 1 improves, for example, sleep by causing a subject user E lying on his/her back on a bed 5 to listen to or feel a sound generated from the loudspeakers 51, 52.

An electrode of the sensor 11 is attached to the forehead of the subject user E so as to detect a brain wave (α wave, β wave, δ wave, θ wave, etc.) of the subject user E. The sensor 12 is worn on the left wrist of the subject user E to detect, for example, a change in pressure of a radial pulse, that is, a pulse wave. The pulse wave is synchronized with heartbeat, and hence the sensor 12 results in detecting heartbeat indirectly. Further, the sensor 13 for detecting an acceleration is provided between the head of the subject user E and a pillow, and the sensor 13 detects a body motion, specifically, breathing, heartbeat, and the like of the subject user E. Detected signals of the sensors 11, 12, 13 are supplied to the sound generator device 20.

Note that, although the sensor 11 is provided in only one portion of the forehead of the subject user E in FIG. 1, the sensor 11 may be provided in a plurality of portions. Further, the detected signals of the sensors 11, 12, 13 are transmitted to the sound generator device 20 via cables for convenience in FIG. 1, but the detected signals may be transmitted thereto wirelessly. In the case where the sensor 11 can detect heartbeat, the sensor 12 may be omitted.

The sound generator device 20 estimates the mind and body state of the subject user E by processing the detected signals of the sensors 11, 12, 13 and controls a plurality of sound generator units in accordance with the estimated mind and body state. The sound generator device 20 is, for example, a mobile terminal, a personal computer, or the like, and a plurality of functional blocks described later are constructed when a CPU executes a program, installed in the sound generator device 20 in advance. Specifically, for example, the sound generator device 20 includes a control unit, a storage unit, a communication unit, an operation unit, and a display unit. The control unit is, for example, a CPU, and operates based on a program stored in the storage unit. The storage unit includes an information recording medium such as a hard disk, a ROM, and a RAM, which stores a program to be executed by the control unit. The communication unit is a network interface, and transmits and receives information via a network in response to a command from the control unit. The operation unit includes an interface such as a keyboard, a mouse, and a button, and outputs, in response to a command operation of the user, the content of the command operation to the control unit. The display unit is, for example, a liquid crystal display, a CRT display, or an OLED display, and displays information based on the command from the control unit. The control unit, the storage unit, the communication unit, the operation unit, and the display unit are connected to each other via a bus. The program to be processed by the control unit may be provided by being downloaded via a network, for example, or may be provided by various computer-readable information recording media such as a CD-ROM and a DVD-ROM. Further, for example, the sound generator device 20 may be formed by an integrated circuit (for example, a tone generator semiconductor chip).

The loudspeakers 51, 52 are arranged at positions which allow the subject user E lying on his/her back to listen to a stereo sound. Of those loudspeakers 51, 52, the loudspeaker 51 amplifies a stereo left (L) signal output from the sound generator device 20 with a built-in amplifier and emits a sound. Similarly, the loudspeaker 52 amplifies a stereo right (R) signal output from the sound generator device 20 with a built-in amplifier and emits a sound. Note that, although there may be a configuration of allowing the subject user E to listen to a sound through headphones, a configuration using the loudspeakers 51, 52 is described in this embodiment.

Figure 2:
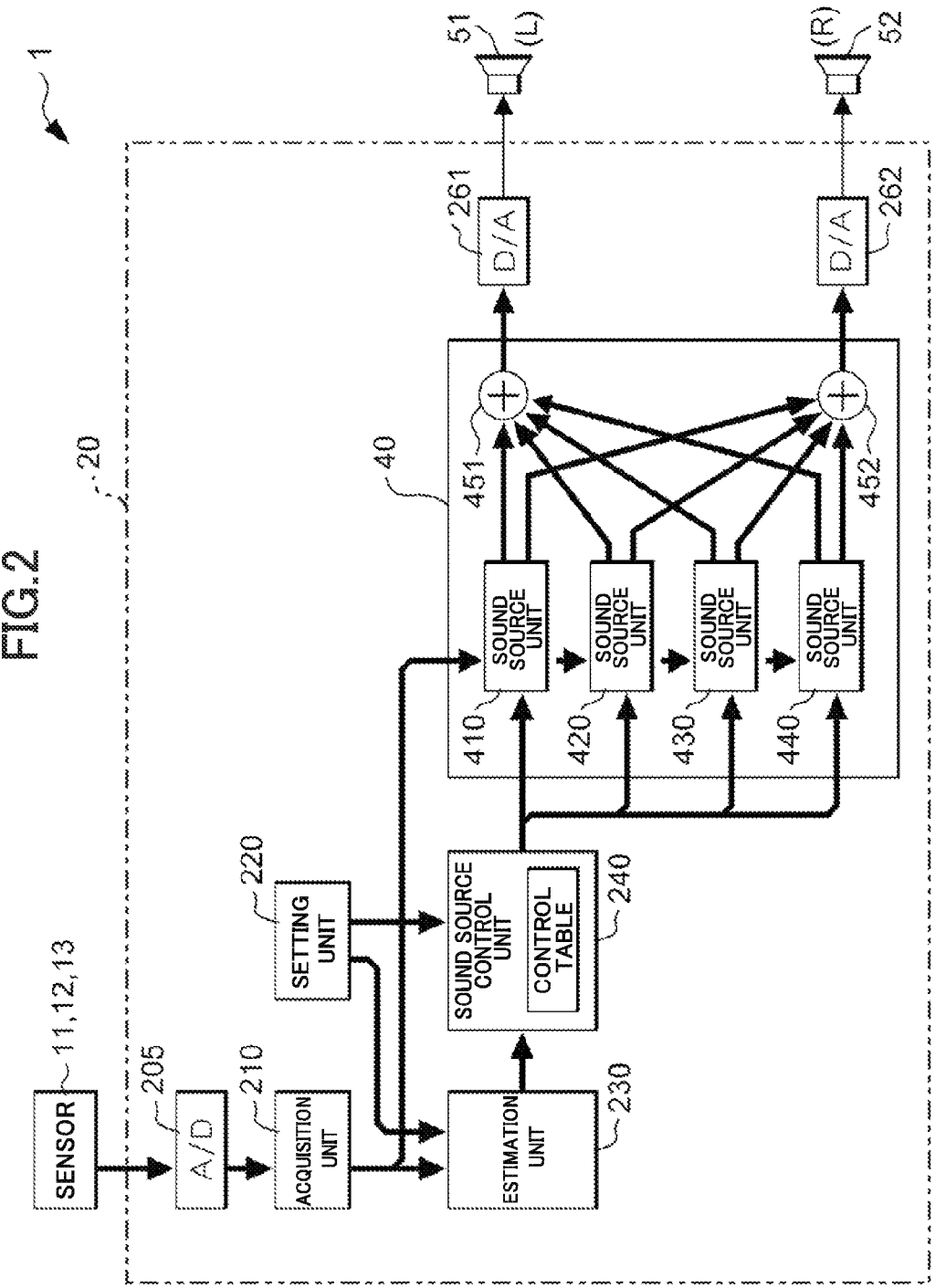
FIG. 2 is a block diagram illustrating a functional configuration of the sound generator device.

FIG. 2 is a diagram illustrating a configuration of functional blocks mainly in the sound generator device 20 of the system 1. As illustrated in FIG. 2, the sound generator device 20 includes an A/D conversion unit 205, an acquisition unit 210, a setting unit 220, an estimation unit 230, a sound generator control unit 240, a sound generator 40, and D/A converters 261, 262. Of those, the functional blocks other than the A/D conversion unit 205 and the D/A converters 261, 262 may be constructed when the above-mentioned program is executed. Further, in this embodiment, the sound generator 40 may include four sound generator units 410, 420, 430, 440. The sound generator (unit) 40 may be formed by a software sound generator that is realized by executing, a program stored in the storage unit using such as CPU, or may be formed by a hardware sound generator such as a sound generator LSI.

The A/D conversion unit 205 converts detected signals of the sensors 11, 12, 13 into digital signals, and the acquisition unit 210 temporarily stores the converted digital signals in an internal memory and supplies the signals to the estimation unit 230 and the sound generator 40, respectively.

On the other hand, the setting unit 220 performs various settings, and specifically sets an object, that is, what is to be improved by the sound generator device 20. As to the object, various objects may be set as described later, and herein, a description is made assuming that the object of "improvement of sleep" is set. Further, the setting unit 220 sets a wake-up time in addition to an object.

In this embodiment, in the case where the object of the "improvement of sleep" is set, the estimation unit 230 estimates the mind and body state from complete rest via sound sleep to wake-up of the subject user E in five stages: "excitation", "wakefulness", "light sleep", "deep sleep", and "rapid eye movement (REM) sleep" based on the detection results of the sensors 11, 12, 13. More specifically, the state in which a body motion changes as in a state immediately after the start of detection is defined as "excitation"; the state in which a β wave is dominant in spite of complete rest with a relatively inactive body motion is defined as "wakefulness"; the state in which a θ wave appears is defined as "light sleep"; the state in which a δ wave appears is defined as "deep sleep"; and the irregular state in which breathing is shallow in spite of the appearance of a θ wave is defined as "REM sleep". In this estimation, various other known procedures may be used. Note that, the "light sleep" and "deep sleep" may also be classified as the "non-REM sleep".

Further, the estimation unit 230 specifies a control mode from the estimated mind and body state and supplies information on the control mode to the sound generator control unit 240. In the control mode in this embodiment, six modes: "relaxation", "sleep onset", "good sleep", "ambient", "wake-up", and "MUTE" are assumed. Note that, which control mode is specified with respect to the estimated mind and body state is described later.

The sound generator control unit 240 determines a control pattern corresponding to control contents of the sound generator 40 in accordance with the object set by the setting unit 220 and the control mode specified by the estimation unit 230. When the sound generator control unit 240 makes this determination, the sound generator control unit 240 refers to a control table which is stored in advance.

FIG. 3 is a diagram showing an example of the control table. FIG. 3 shows an example in which the object of "improvement of sleep" is set, and a control pattern is defined for each control mode. Specifically, in this embodiment, the control pattern is classified into four kinds: hypersonic, binaural beats, a natural sound, and music. Of those kinds, the hypersonic is output by the sound generator unit 410. Further, the binaural beats, natural sound, and music are output by the sound generator unit 420, the sound generator unit 430, and the sound generator unit 440, respectively.

In each control mode, a symbol "○" indicates that the corresponding sound generator unit is activated for use, and a symbol "×" indicates that the corresponding sound generator unit is inactivated for use.

Of parameters associated with the symbol "○", regarding the binaural beats, a range of a frequency difference between a left signal and a right signal is designated, and regarding the tempo control of the natural sound and music, it is designated how lower the tempo of a sound to be output is set compared to the heart rate (beats/min) of the subject user E. For example, when the tempo control is "−3", the reproduction at a tempo lower by 3 than the heart rate of the subject user E is designated, and when the tempo control is "twice", the reproduction at a tempo twice that of the heart rate of the subject user E is designated. Further, the beat control of the natural sound and music designates the beat of a sound to be reproduced. Regarding the volume, the magnitude of a sound to be output is designated.

Referring again to the description of FIG. 2, when the four sound generator units 410, 420, 430, 440 in the sound generator 40 output signals of a sound in accordance with the designated parameters in two stereo channels in a digital form when the sound generator units are activated by the sound generator control unit 240.

A mixer 451 mixes (adds up) left (L) signals respectively output from the sound generator units 410, 420, 430, 440, and similarly, a mixer 452 mixes right (R) signals respectively output from the sound generator units.

The D/A converter 261 converts the left (L) signal mixed by the mixer 451 into an analog signal and outputs the analog signal. Similarly, the D/A converter 262 converts the right (F) signal mixed by the mixer 452 into an analog signal and outputs the analog signal.

Next, each of the four sound generator units 410, 420, 430, 440 of the sound generator 40 is described. Firstly, the sound generator unit (I) 410 corresponding to a third sound generator unit, which imparts hypersonic effects, is described. Each of the four sound generator units 410, 420, 430, and 440 may be formed by a functional unit realized by executing an algorithm of the above-mentioned software sound generator, or may be formed by a logic circuit constituting the above-mentioned hardware sound generator.

When an audible sound and a high-frequency inaudible sound are generated, a human listens to the audible sound by the ear while feeling the inaudible sound by the body surface. It is said that when the human listens to and feels a sound in this manner, the following healing effects are realized. The body of the human reacts to the sounds so as to activate the brain, to increase an α wave and to reduce stress. As a result, the mind and body are healed. The sound generator unit 410 provides such effects.

Note that, an audible sound to an inaudible sound can be generated in a frequency range of, for example, 20 Hz to 96 kHz simply by reproducing data recorded at a sampling frequency of 192 kHz. However, in this case, there may be a problem that a great amount storage capacity is required, and in addition, rerecording may be newly required because existing sound recordings cannot be used due to its maximum frequency of about 24 (20) kHz. In order to solve this problem, the sound generator unit 410 in this embodiment may be configured as follows.

Figure 4:
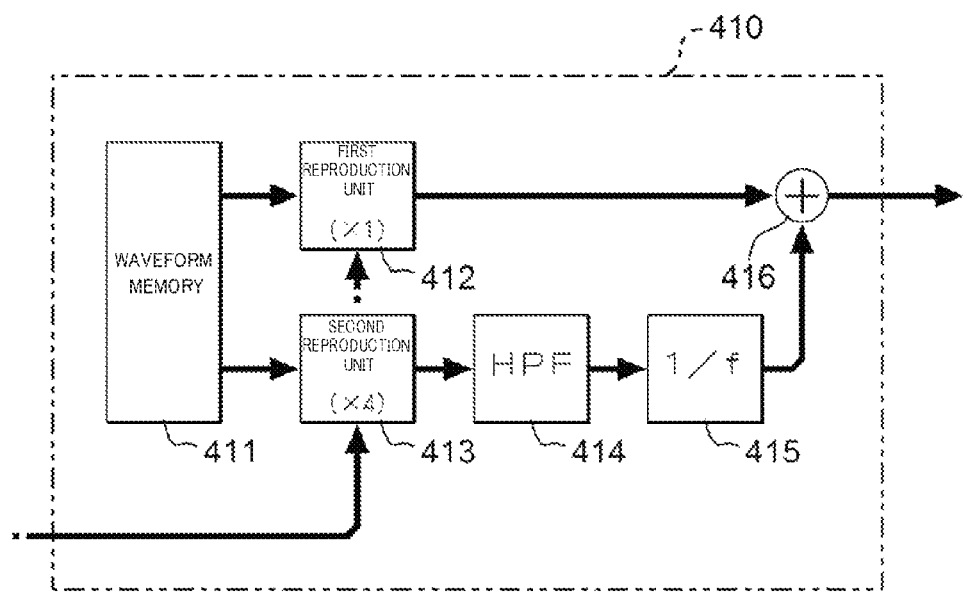
FIG. 4 is a block diagram illustrating an example of a configuration of a sound generator unit (I) of the sound generator device.

FIG. 4 is a block diagram illustrating a configuration of the sound generator unit 410. As illustrated in FIG. 4, the sound generator unit 410 includes a waveform memory 411, a first reproduction unit 412, a second reproduction unit 413, a high-pass filter (HPF) 414, a 1/f filter 415, and an adder (mixing unit) 416. The waveform memory 411 stores data recorded in a frequency band of 20 Hz to 24 kHz.

The first reproduction unit 412 reads and outputs data from the waveform memory 411 at a single speed (equal speed), that is, in accordance with the sampling frequency at a time of recording. Therefore, the data read by the first reproduction unit 412 has a frequency band of 20 Hz to 24 kHz when converted into analog data by the D/A converters 261, 262.

The second reproduction unit 413 reads and outputs data from the waveform memory 411 at a quadruple speed. Therefore, the data read at a quadruple speed has a frequency band of 80 Hz to 96 kHz when converted into analog data. In the frequency band, components of about 20 kHz or less are not necessary and hence cut by the HPF 414. The 1/f filter 415 adjusts an amplitude of the data read at a quadruple speed so that a spectrum component with the components of 20 kHz or less cut becomes 1/f.

The adder 416 adds up the data read at a single speed (equal speed) by the first reproduction unit 412 and the data read at a quadruple speed of which amplitude is adjusted, and outputs the result. Note that, the added data is assigned to the left (L) and the right (R) by a panning circuit (not shown) and output from the sound generator unit 410.

Figure 5:
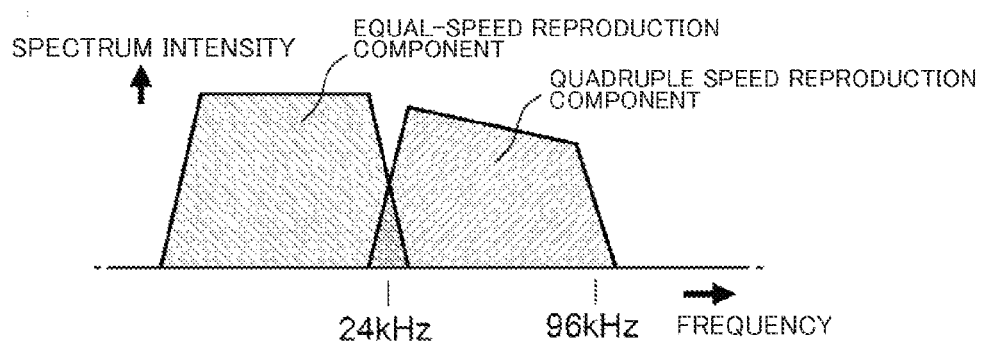
FIG. 5 is a graph showing an example of a frequency spectrum output by the sound generator unit (I).

As shown in FIG. 5, the sound generator unit 410 outputs, in a mixed state, an audible frequency component (equal-speed reproduced component) of 20 Hz to 24 kHz and an inaudible frequency component of 20 kHz to 96 kHz with components of 20 kHz or less cut, of quadruple-speed reproduced component, and hence healing effects by hypersonic can be expected. Further, the sound generator unit 410 may use existing sound recordings of 20 Hz to 24 kH so as to suppress the storage capacity of the waveform memory 411.

Note that, in order to extend the existing sound recordings up to a high-frequency inaudible band, there is given a procedure using distortion or a conversion table. Further, instead of sound recordings, a synthesizer sound generator such as an FM sound generator may be used to generate a signal in an audible band together with a signal in an inaudible band.

Next, the sound generator unit (II) 420 which outputs binaural beats is described.

The brain wave has a low frequency component of about 1 Hz to 40 Hz. Such a frequency is hardly audible to a human ear directly. However, when a stereo sound having a frequency difference is given to both ears, that is, for example, when a frequency of 100 Hz is given to one ear and a frequency of 110 Hz is given to the other ear, a the difference of the frequency of 10 Hz is recognized in the brain, and the brain wave attempts to be in tune with the frequency difference. The binaural beats are to give the frequency difference. When the frequency difference is set to, for example, a frequency of an α wave, the brain wave becomes close to the frequency difference, and hence it is expected that a relaxed state is obtained.

Figure 6:
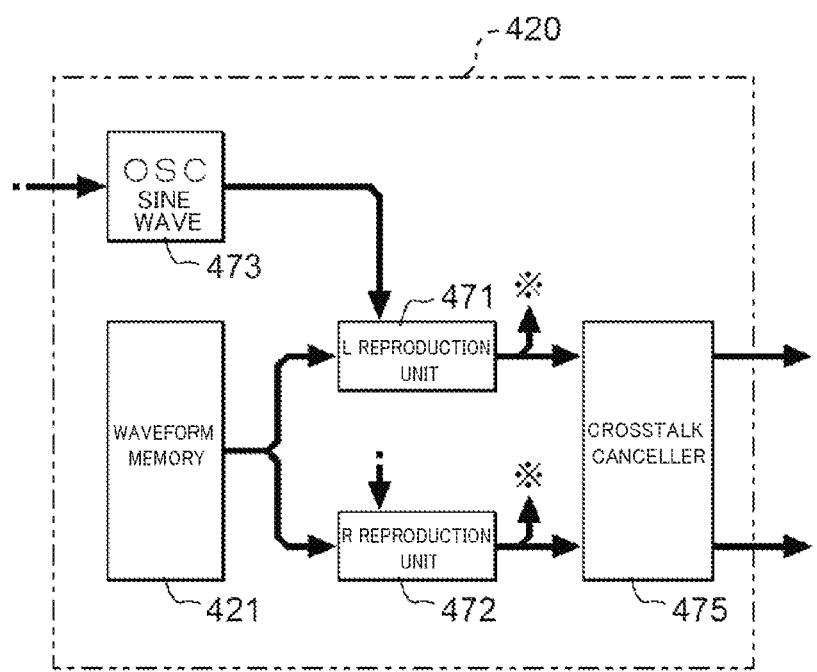
FIG. 6 is a block diagram illustrating an example of a configuration of another sound generator unit (II).

FIG. 6 is a block diagram illustrating a configuration of the sound generator unit 420. As illustrate in FIG. 6, the sound generator unit 420 includes a waveform memory 421, an oscillator (OSC) 473, an L reproduction unit 417, an R reproduction unit 472, and a crosstalk canceller 475.

The waveform memory 421 stores waveform data to be a reference signal for providing a frequency difference. The oscillator 473 is supplied with a parameter showing a target frequency difference from the sound generator control unit 240. The oscillator 473 oscillates a sine wave having a waveform in accordance with the frequency difference indicated by the parameter.

The L reproduction unit 471 reproduces waveform data from the waveform memory 421 at a pitch that is based on a signal level of the sine wave oscillated by the oscillator 473, whereas the R reproduction unit 472 reads and reproduces waveform data at a pitch that is based on a signal level of an inverted sine wave.

Figure 7:
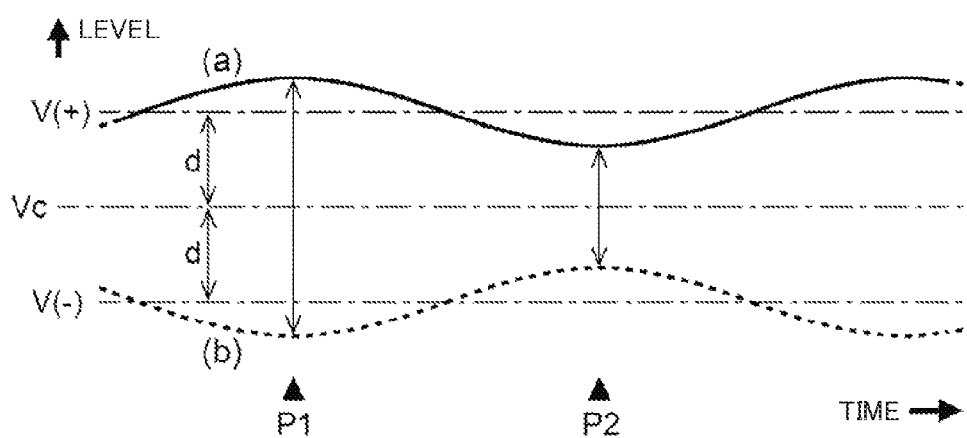
FIG. 7 is a graph showing an example of a variation in a reproduction pitch in the sound generator unit (II).

FIG. 7 is a graph showing a relationship between the sine waves oscillated by the oscillator 473 and the change in pitch by the L reproduction unit 471 and the R reproduction unit 472.

In FIG. 7, (a) represents a sine wave oscillated by the oscillator 473 in which an amplitude center V (+) is offset by "d" to the positive side from a reference level Vc. The L reproduction unit 471 puts forward a reproduction pitch of the waveform data by a difference between the reference level Vc and the level of the sine wave. (b) represents a waveform obtained by inverting the sine wave oscillated by the oscillator 473 with respect to the reference level Vc, and an amplitude center V (−) thereof is offset by "d" to the negative side from the reference level Vc. The R reproduction unit 472 delays the reproduction pitch of the waveform data by a difference between the reference level Vc and the level of the inverted sine wave.

In this case, the frequency difference in the binaural beats becomes maximum at a timing P1 when the difference in signal level between the sine wave and the inverted sine wave becomes maximum, and becomes minimum at a timing P2 when the difference in signal level between the sine wave and the inverted sine wave becomes minimum. Thus, it is appropriate that the oscillator 473 oscillates a sine wave so that the difference in signal level between the sine wave and the inverted sine wave at the timing P1 reaches a maximum value in a frequency range designated by the sound generator control unit 240 and so that the difference in signal level between the sine wave and the inverted sine wave at the timing P2 reaches a minimum value in the frequency range.

Note that, it is also possible to output a tone signal with a single frequency of, for example, 100 Hz, and to increase the frequency of the tone signal by an amount that is based on the level of the sine wave and decrease the frequency of the tone signal by an amount that is based on the level of the inverted sine wave, instead of reading waveform data from the waveform memory 421. Further, the frequency of the sine wave may be set appropriately, and for example, a triangle wave may be used instead of the sine wave. The read pitch of one of the L reproduction unit 471 and the reproduction unit 472 may be fixed, and the read pitch of the other may be varied depending on the signal level of a sine wave with a double amplitude.

In this embodiment, the sleep state of the subject user E is improved with a sound generated from the loudspeakers 51, 52 as described above. In this configuration, a kind of crosstalk occurs in which not only a sound of the left (L) generated from the loudspeaker 51 but also a sound of the right (R) generated from the loudspeaker 52 reaches the left ear of the subject user E. The same also applies to the right ear of the subject user E. In this state, the right and left ears of the subject user E may not listen to sounds having different frequencies correctly in the binaural beats.

Thus, in this embodiment, the crosstalk canceller 475 is provided for the case using the loudspeakers 51, 52. Specifically, the crosstalk canceller 475 adds a component for cancelling the sound of the right (R) generated from the loudspeaker 52, which reaches the left ear of the subject user E, to waveform data read from the L reproduction unit 471 when the subject user E lies on his/her back on the bed 5 as illustrated in FIG. 1. Similarly, the crosstalk canceller 475 adds a component for cancelling the sound of the left (L) generated from the loudspeaker 51, which reaches the right ear, to waveform data read from the R reproduction unit 472.

Thus, in the sound generator unit 420, even in the case using the loudspeakers 51, 52, the sound of the left (L) generated from the loudspeaker 51 and the sound of the right (R) generated from the loudspeaker 52 respectively reach the left ear and the right ear in a separated manner. Therefore, the brain is allowed to recognize a frequency difference.

Note that, in the case where the subject user E wears headphones (not shown), the waveform data read by the L reproduction unit 471 and the waveform data read by the R reproduction unit 472 may be output while bypassing the crosstalk canceller 475 as indicated by a symbol "*" in FIG. 6.

Figure 8:
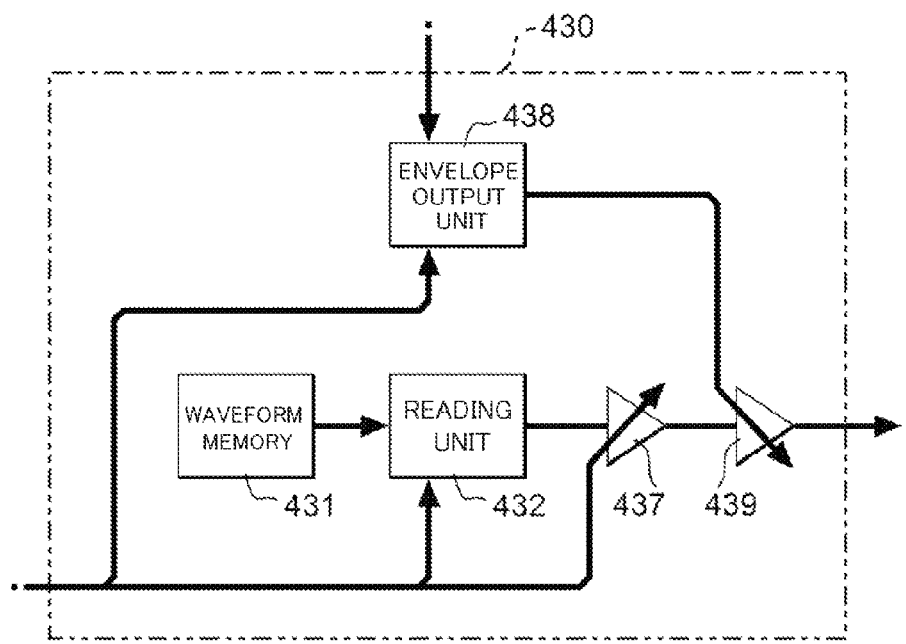
FIG. 8 is a block diagram illustrating an example of a configuration of still another sound generator unit (III).

Next, the sound generator unit (III) 430 corresponding to a first sound generator unit, which outputs a natural sound, is described. FIG. 8 is a block diagram illustrating a configuration of the sound generator unit 430. As illustrated in FIG. 8, the sound generator unit 430 includes a waveform memory 431, a reading unit 432, multipliers 437, 439, and an envelope output unit 438. The waveform memory 431 stores waveform data of, for example, a wind sound, a wave sound, and river babble. The reading unit 432 reads waveform data in a set reading section. The multiplier 437 multiplies the read waveform data by a coefficient corresponding to a volume supplied from the sound generator control unit 240 and outputs the result.

In the sound generator unit 430, the storage capacity of the waveform memory 431 is limited in a configuration of simply reading waveform data repeatedly, and hence reproduction tends to become monotonous. Therefore, when the subject user E listens to such reproduced sound for a long period of time, the subject user E is bored or annoyed with unnaturalness. Thus, the mind and body state opposite to the state of inducing deep sleep in the subject user E is caused.

Then, in this embodiment, the reading unit 432 has a configuration of reading waveform data as follows. That is, firstly, the reading unit 432 reads waveform data while dividing the wave form data into a plurality of reading sections having the range from starting the reading to finishing the reading. In this case, the position of the reading section and time length are set at random. Secondly, the reading unit 432 reads the waveform data so as to overlap joint portions of the reading sections each other and to cause fade-out at the end of a certain reading section and fade-in at the start of a subsequent reading section. Thirdly, the reading unit 432 multiplies waveform data that are read for respective reading sections by different coefficients inside the reading unit 432 and outputs the result. Fourthly, the reading unit 432 reads that waveform data so that a reproduction pitch is fluctuated with 1/f.

Figure 9:
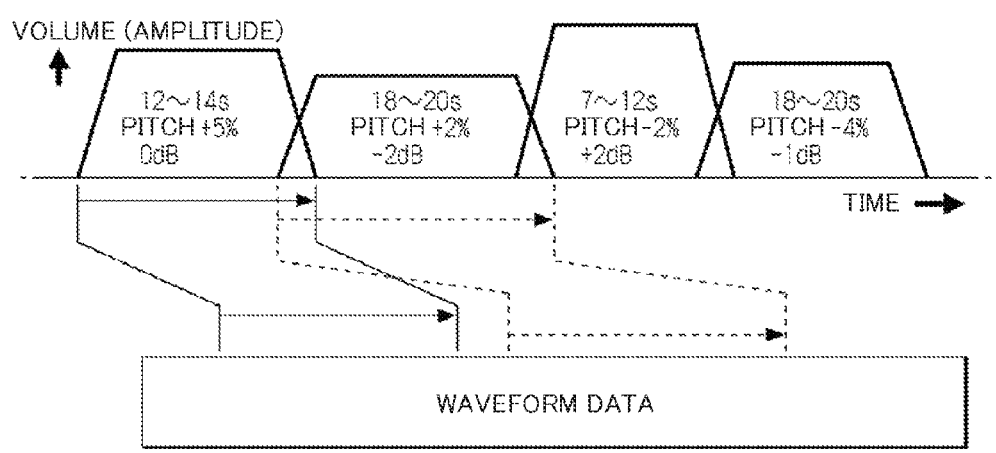
FIG. 9 is a graph showing an example of reading of the sound generator unit (III).

FIG. 9 is a graph showing a relationship of waveform data read from a section which has been set at random, a reproduction pitch, and an amplitude. In FIG. 9, for example, a portion indicated by 12s~14s indicates that the portion is read from a section of 12-14s of the waveform data, the reproduction pitch is +5% of the waveform data, and the amplitude is 0 db with respect to the amplitude of the waveform data.

Due to the fade-in and fade-out, the unnaturalness in joint portions of reading sections is alleviated. Further, a volume and a reproduction pitch are fluctuated, and hence compared with the simple repetition of reproduction, a boring feeling and an annoying feeling caused by unnaturalness are prevented from being given to the subject user E.

Note that, the reading unit 432 may read data on a regular basis instead of reading data at random. This is because, even when the reading unit 432 reads data on a regular basis, if a period of a regular pattern is long, the subject user E can be prevented from feeling the regularity.

Further, a sound to be reproduced by the sound generator unit 430 may be music or the like without being limited to a wind sound, a wave sound, and river babble. When the recorded waveform data is stored in the waveform memory 431 while the waveform data is reproduced at a tempo that is based on the heart rate in the case where sound recordings such as music are reproduced, it is considered that a person who has listened to this sound can easily fall asleep. Therefore, in the sound generator unit 430, the reading unit 432 reproduces a sound at a tempo lower by a value designated by the sound generator control unit 240 than the heart rate of the subject user E.

Note that, the sound to be reproduced by the sound generator unit 430 may include music and the like, and hence the sound to be reproduced by the sound generator unit 430 is not a natural sound in a strict sense. However, the expression of reproducing a natural sound is used so as to discriminate the sound generator unit 430 from the sound generator unit 440.

The sound generator unit 430 has a configuration capable of controlling the amplitude of the waveform data that are read with an envelope that is based on heartbeat so as to cause the subject use E to feel heartbeat. Specifically, the envelope output unit 438 outputs pulse detected by the sensor 12 or an envelope waveform that is based on heartbeat detected by the sensor 13, as indicated by a solid line in FIG. 10. In this case, the envelope output unit 438 outputs an envelope waveform at a tempo that is lower by a value designated by the control table in the sound generator control unit 240 than the detected heart rate (pulse rate). The multiplier 439 multiplies the waveform data, which has been multiplied by a coefficient by the multiplier 437, by the envelope waveform and outputs the result.

Thus, when the amplitude of the waveform data is controlled with the envelope that is based on heartbeat, the subject user E is likely to feel his/her heartbeat although a music property of the waveform data is lost. Therefore, the subject user E is considered to easily fall asleep.

Figure 10:
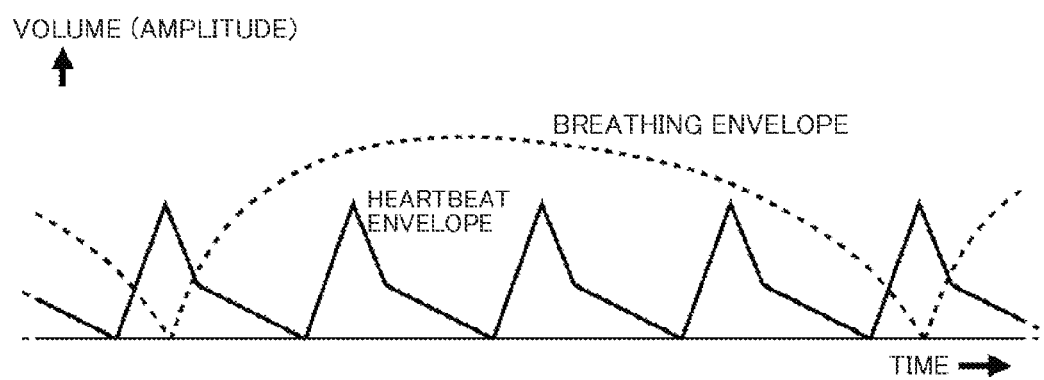
FIG. 10 is a graph showing an example of an envelope provided in the sound generator unit (III).

Note that, the sound generator unit 430 may have a configuration of controlling the amplitude of the read wave form data with an envelope that is based on breathing instead of heartbeat. Specifically, the envelope output unit 438 outputs an envelope waveform that is based on breathing of the subject user E as indicated by a broken line in FIG. 10. Alternatively, it is said that breathing changes in tune with heartbeat (pulse), and during sleep, breathing tends to occur once every four heartbeats, for example, as shown in FIG. 10. Using this tendency, the envelope output unit 438 outputs an envelope waveform having a frequency of ¼ with respect to the envelope waveform that is based on heartbeat. In this configuration, the amplitude of waveform data is controlled that is based on breathing, and hence it is considered that the subject user E feels his/her breathing and easily falls asleep.

It is considered that, with the sound generator unit 430, the subject user E is prevented from feeling bored or being annoyed with unnaturalness, and a sound is reproduced at a tempo that is based on heartbeat or breathing, so that the subject user E may easily fail asleep.

Note that, the sound generator unit 430 may also have a configuration other than reading of waveform data, and for example, a signal (white noise) obtained by a random number generator may be used. In this case, the intensity of the signal is flat with respect to a frequency, and hence the signal may be filtered with a filter so as to have characteristics of a 1/f spectrum on a high-pass side. Further, the signal may be subjected to amplitude modulation with 1/f so as to have characteristics of a 1/f spectrum also on a low-pass side.

Further, the sound generator unit 430 may have a configuration of reproducing musical instrument digital interface (MIDI) data or a configuration using a synthesizer sound generator such as an FM sound generator. In such a configuration, it is preferred that an amplitude, a tempo, and a tone color be fluctuated with 1/f while a sound is reproduced at a tempo of heartbeat or breathing. The data amount of the MIDI data is smaller than that of waveform data and hence a great amount of music can be stored and selected at random. Therefore, the effect of preventing the subject user E from listening to the same sound to be bored is easily obtained. Further, the FM sound generator can easily change a tone color minutely, and hence can generate a sound which is further unlikely to cause the subject user E to be bored.

Figure 11:
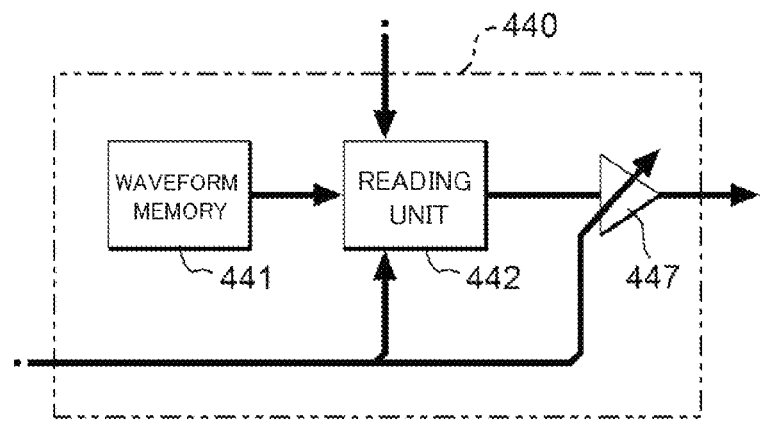
FIG. 11 is a block diagram illustrating an example of a configuration of still another sound generator unit (IV).

Next, the sound generator unit (IV) 440 corresponding so a second sound generator unit, which outputs music, is described. FIG. 11 is a block diagram illustrating a configuration of the sound generator unit 440. As illustrated in FIG. 11, the sound generator unit 140 includes a waveform memory 441, a reading unit 142, and a multiplier 417. The waveform memory 441 stores waveform data of music, and the reading unit 442 reproduces the waveform data at a tempo that is lower by a value designated by the sound generator control unit 240 than the heart rate detected by the sensors 12, 13 and at a designated beat. The multiplier 447 multiplies the read waveform data by a coefficient corresponding to the volume supplied from the sound generator control unit 240 and outputs the result.

Note that, in the sound generator unit 440, the reading unit 442 may read waveform data so that a tempo is fluctuated with 1/f or may multiply the read waveform data by a coefficient inside the reading unit 442 so that the volume is fluctuated with 1/f and output the result. Further, in the same way as in the reading unit 432 of the sound generator unit 430, the reading unit 442 of the sound generator unit 440 may be configured to divide into a plurality of reading sections having a range from a reading start to a reading end, and the position of the reading section and time length may be set at random, thereby reading waveform data.

In the sound generator unit 440, it is considered that the state of the subject user E can be shifted to a relaxed state so that the subject user E can easily fall asleep by reproducing music at a tempo in accordance with heartbeat or the like, and on the other hand, the state of the subject user E can be shifted to a wakefulness state opposite to the relaxed state by reproducing music at a up-tempo. Further, the sound generator unit 440 can output a sound which does not bore or annoy the subject user E because the reproduction tempo, volume, and the like are fluctuated.

Note that, regarding the output of the multiplier 439 in the sound generator unit 430 and the output of the multiplier 447 in the sound generator unit 440, two channels of the outputs may be processed in the left (L) and the right (R) from reading, or the outputs may be divided into the left (L) and the right (R) by the panning circuit (not shown).

Figure 12:
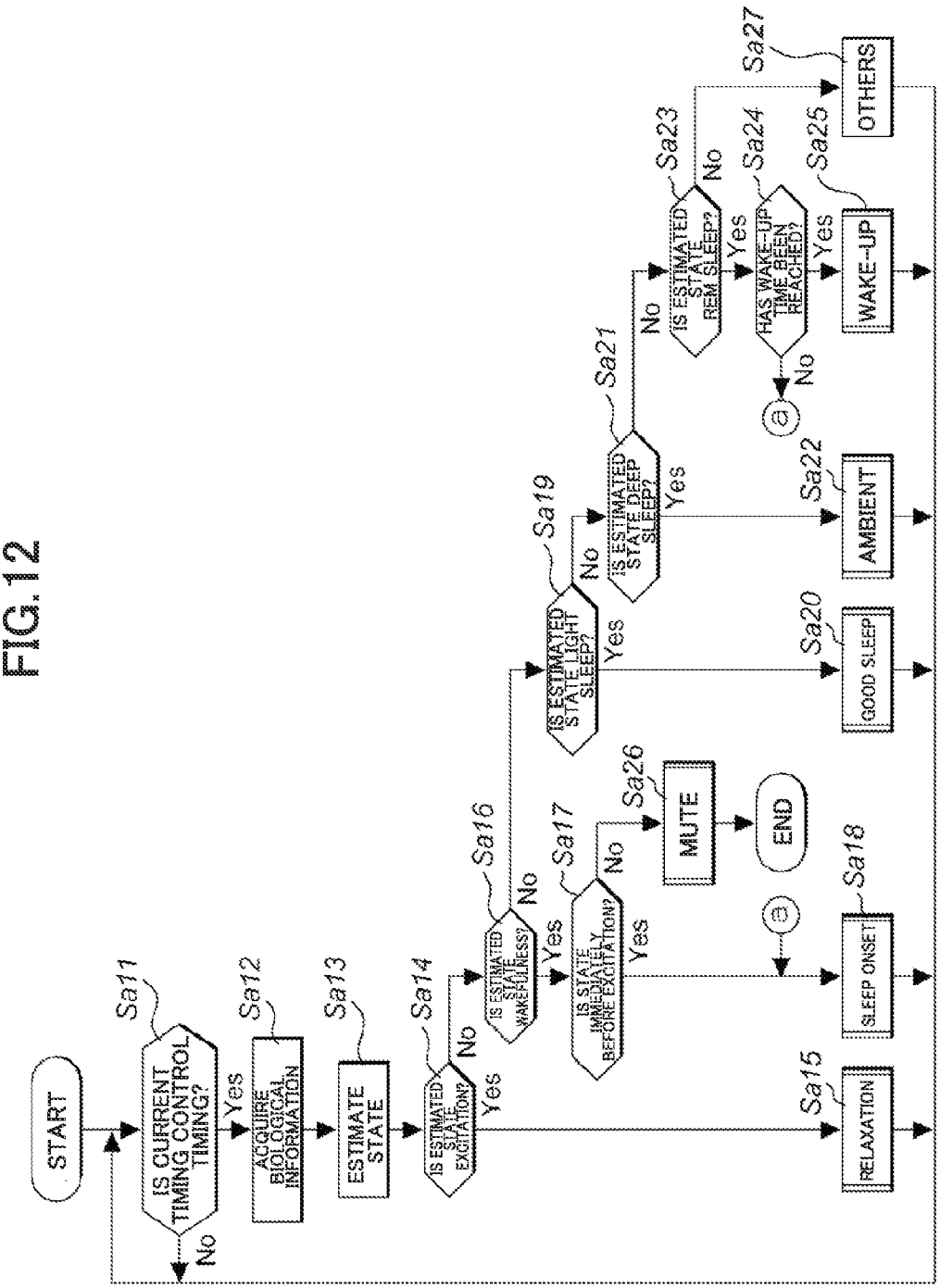
FIG. 12 is a flowchart illustrating an operation of the sound generator device.

Next, the processing operation of the sound generator device 20 according to this embodiment is described. FIG. 12 is a flowchart illustrating the operation of the sound generator device 20.

When the setting unit 220 sets "improvement of sleep" as an object in the sound generator device 20, the estimation unit 230 determines whether or not the current timing is a control timing (Step Sa11). The subsequent operations are repeatedly performed at a predetermined time interval in this embodiment. If this interval is, for example, 5 minutes, the estimation unit 230 determines whether or not 5 minutes have elapsed from the previous execution. When the determination result is "No", the processing procedure returns to Step Sa11. Therefore, the subsequent processing is not performed until the predetermined period of time elapses from the previous execution.

When the predetermined period of time elapses from the previous execution, and the determination result becomes "Yes", the estimation unit 230 acquires detected signals of the sensors 11, 12, 13 from the acquisition unit 210 (Step Sa12). The detected signals to be acquired may be, for example, those which are accumulated in the internal memory during a period from the previous execution to the current execution or those which are accumulated in the internal memory during the immediately previous one minute. Next, the estimation unit 230 processes/analyzes the acquired detected signals to estimate which of the five stages the mind and body state of the subject user E corresponds to (Step Sa13).

Then, the estimation unit 230 branches the processing depending on the estimated mind and body state by the subsequent steps Sa14, Sa16, Sa19, Sa21, and Sa23. Specifically, firstly, when the estimated mind and body state is "excitation" (the determination result of Step Sa14 is "Yes"), the estimation unit 230 sets the control mode of the sound generator control unit 240 to "relaxation" (Step Sa15).

When the control mode is set to "relaxation", the sound generator control unit 240 controls the sound generator 40 in a control pattern corresponding to the "relaxation" with reference to the control table shown in FIG. 3. Specifically, the sound generator control unit 240 activates the sound generator units 410, 420, 440 and inactivates the sound generator unit 430. Thus, a mixed sound of hypersonic, binaural beats, and music is output from the loudspeakers 51, 52.

Of those, it is expected that the state of the subject user E is shifted to the relaxed state by the hypersonic. Further, the binaural beats are controlled so that a frequency difference between the left (L) and the right (R) changes in a range of 7 Hz to 14 Hz in accordance with the control table. The subject user E who has listened to the binaural beats controlled as explained above recognizes the frequency difference in the brain. The frequency difference in the range of 7 Hz to 14 Hz is almost the same as an α wave in the brain wave, and hence it is expected that the state of the subject user E is shifted to the relaxed state.

On the other hand, music is reproduced at a tempo (0.05 Hz in terms of a frequency) that is lower by "3" than the heart rate detected from the subject user E by the sensors 12, 13. For example, when the heart rate is 60 beats per minute, music is reproduced with the tempo being set to "57" that is lower by "3" than the heart rate. Further, the music to be reproduced in this case is reproduced in quadruple time, and the volume is set to "medium". Thus, the heart rate is guided so as to approach the tempo of the reproduced music, and hence it is expected that the state of the subject user E is shifted to the relaxed state.

Note that, the period of breathing changes with respect to heartbeat (or conversely, the period of heartbeat changes in synchronization with breathing), and hence it is expected that the state of the subject user E is shifted to a further relaxed state by setting music to be reproduced in, for example, quadruple time so as to be adjusted to the rhythm of breathing.

It is considered that the mind and body state of the subject user E who has listened to such a synthetic sound of hypersonic, binaural beats, and music is eventually shifted from "excitation" to "wakefulness" which is a relaxed state by one stage. Note that, after Step Sa15, the processing procedure returns to Step Sa11.

On the other hand, when the estimated mind and body state is not "excitation" but "wakefulness" (the determination result in Step Sa16 is "Yes"), the estimation section 230 secondly determines whether or not the mind and body state estimated immediately before has been "excitation" (Step Sa17).

In this embodiment, as the case in which the estimated mind and body state reaches "wakefulness", two cases are assumed. The two cases include the case in which the mind and body state is shifted from "excitation" to "wakefulness" and the case in which the mind and body state is shifted from "REM sleep" to "wakefulness" as described later. The control mode is varied with respect to the respective cases. Therefore, in Step Sa17, it is determined which case the current case corresponds to.

In the case where the mind and body state is shifted not from "excitation" but from "REM sleep" to "wakefulness" (the determination result of Step Sa17 is "No"), the estimation unit 230 sets the control mode of the sound generator control unit 240 to "MUTE" (Step Sa26). As shown in FIG. 3, the "MUTE" is a control mode for inactivating all the sound generator units 410, 420, 430, 440, and hence a sound generated from the loudspeakers 51, 52 is suspended. After that, the operation of the sound generator device 20 is completed.

On the other hand, in the case where the mind and body state is shifted from "excitation" to "wakefulness" (the determination result in Step Sa17 is "Yes"), the estimation unit 230 sets the control mode of the sound generator control unit 240 to "sleep onset" (Step Sa18).

When the control mode is set to "sleep onset", the sound generator control unit 240 controls the sound generator 40 with a control pattern corresponding to "sleep onset" with reference to the control table. Specifically, the sound generator control unit 240 activates the sound generator units 410, 420, 430 and inactivates the sound generator unit 440. Thus, a mixed sound of hypersonic, binaural beats, and a natural sound is output from the loudspeakers 51, 52.

Of those, the hypersonic is the same as the control mode of "relaxation".

Further, the binaural beats are controlled so that the frequency difference between the left (L) and the right (R) changes in a range of 4 Hz to 7 Hz in accordance with the control table. The frequency difference is almost the same as a θ wave in the brain wave, and hence it is expected that the mind and body state is shifted to deeper sleep.

On the other hand, when the control mode is changed from "relaxation" to "sleep onset", music is switched to a natural sound. The natural sound at this time is reproduced at a tempo which is lower by "3" than the heart rate of the subject user E. For example, when the heart rate further decreases to 57 compared with the number at a time when the control mode is set to "relaxation", the natural sound is reproduced at a tempo of "54" which is lower by "3" than 57. Further, a sound at this time is reproduced in quadruple time, and the volume is set to "small" so as not to hinder the shift to sleep.

It is considered that the mind and body state of the subject user E who has listened to such a mixed sound of hypersonic, binaural beats, and a natural sound is eventually shifted from "wakefulness" to "light sleep" which is a state of initial sleep. Note that, after Step Sa18, the processing procedure returns to Step Sa11.

If the mind and body state is not "excitation" or "wakefulness" but "light sleep" (the determination result in Step Sa19 is "Yes") the estimation unit 230 thirdly sets the control mode of the sound generator control unit 240 to "good sleep" (Step Sa20).

When the control mode is set to "good sleep", the sound generator control unit 240 controls the sound generator 40 with a control pattern corresponding to "good sleep" with reference to the control table, and consequently activates the sound generator units 410, 430 and inactivates the sound generator units 420, 440. Thus, a mixed sound of hypersonic and a natural sound is output from the loudspeakers 51, 52.

Of those, the hypersonic is similar to "relaxation" and "sleep onset" of the control mode.

On the other hand, the natural sound is reproduced at a tempo which is lower by "2" than the heart rate of the subject user E. For example, when the heart rate further decreases to 56 compared with the number at a time when the control mode is set to "sleep onset", the natural sound is reproduced at a tempo of "54" which is lower by "2" than 56.

It is considered that the subject user E has already fallen asleep, but it is considered that the state of the subject user E is shifted from "light sleep" to "deep sleep" which is a deeper sleep state by listening to such a mixed sound of hypersonic and a natural sound. Note that, after Step Sa20, the processing procedure returns to Step Sa11.

If the mind and body state is not "excitation", "wakefulness", or "light sleep" but "deep sleep" (the determination result in Step Sa21 is "Yes"), the estimation unit 230 fourthly sets the control mode of the sound generator control unit 240 to "ambient" (Step Sa22).

When the control mode is set to "ambient", the sound generator control unit 240 controls the sound generator 40 with a control pattern corresponding to "ambient" with reference to the control table, and consequently activates the sound generator unit 410 and inactivates the sound generator units 420, 430, 440. Thus, only hypersonic is output from the loudspeakers 51, 52. It is considered that the subject user E has already fallen into deep sleep, and hence in order to keep this state, only the hypersonic is sufficient. Note that, after Step Sa22, the processing procedure returns to Step Sa11.

If the mind and body state is not "excitation", "wakefulness", "light sleep", or "deep sleep" but "REM sleep" (the determination result in Step Sa23 is "Yes"), the estimation unit 230 fifthly determines whether or not the current time has reached a wake-up time set by the setting unit 220 (Step Sa24).

If the current time is before the wake-up time (the determination result in Step Sa24 is "No"), the sound generator control unit 240 sets the control mode to "sleep onset" again (Step Sa18). On the other hand, if the current time has reached the wake-up time, (the determination result in Step Sa24 is "Yes"), the sound generator control unit 240 sets the control mode to "wake-up" (Step Sa25).

When the control mode is set to "wake-up", the sound generator control unit 240 controls the sound generator 40 with a control pattern corresponding to "wake-up" with reference to the control table, and consequently activates only the sound generator unit 440. Therefore, music is output with a relatively large volume from the loudspeakers 51, 52. Further, music at this time is reproduced at a tempo which is twice a tempo of the heartbeat and in double time. Thus, the subject user E wakes up refreshingly from REM sleep. Note that, after Step Sa25, the processing procedure returns to Step Sa11.

On the other hand, it is considered that, in the case where the mind and body state is not "excitation", "wakefulness", "light sleep", "deep sleep", or "REM sleep" (the determination result in Step Sa23 is "No"), the mind and body state is in a scene which is not assumed in this embodiment. Therefore, for example, processing such as display of an error is performed (Step Sa27), and the processing procedure returns to Step Sa11. Note that, the operation of the sound generator device 20 may be forcefully terminated instead of returning the processing procedure to Step Sa11.

Subsequently, the specific operation of the sound generator device 20 is described with reference to FIG. 13.

Figure 13:
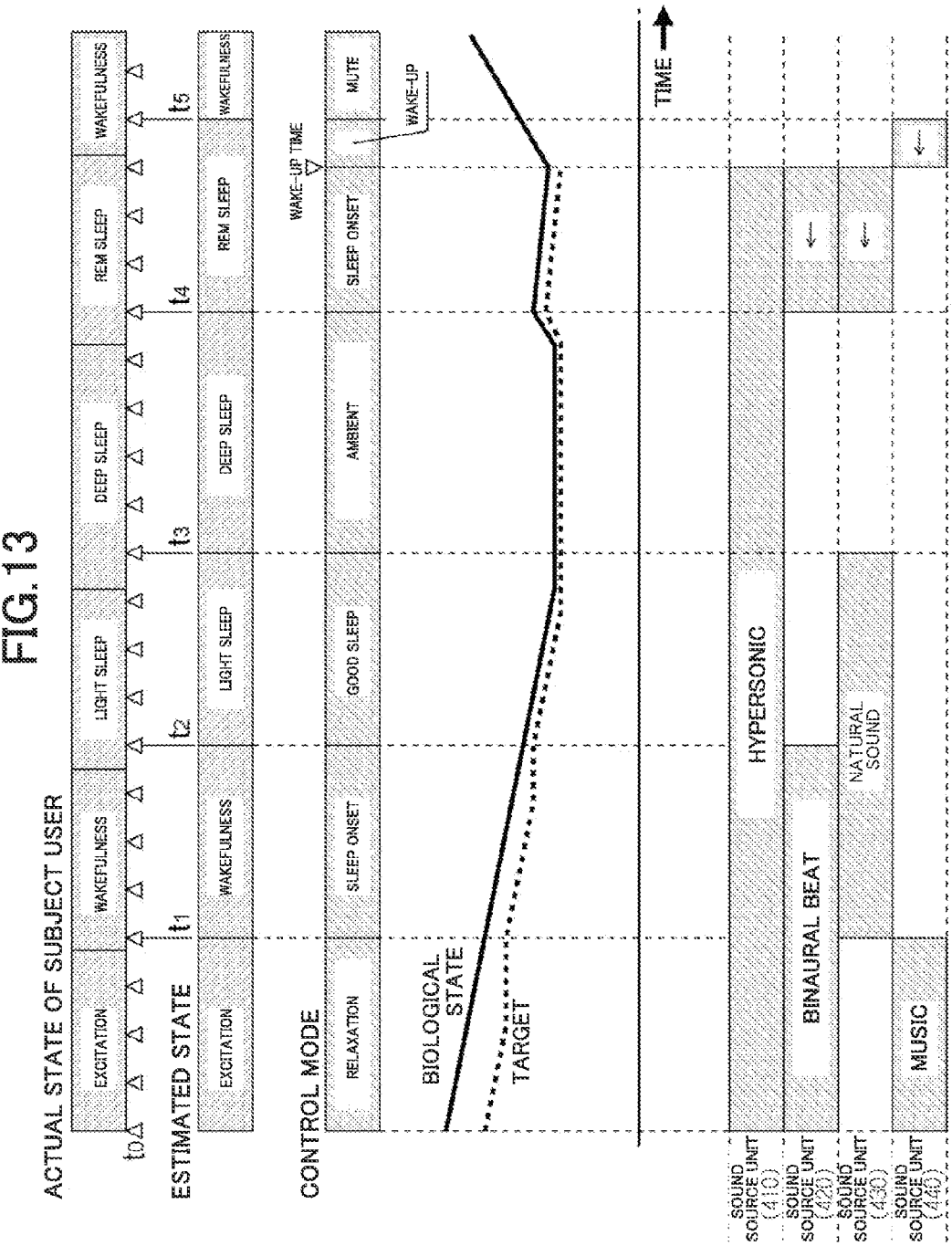
FIG. 13 is a graph showing a specific operation of the sound generator device.

In FIG. 13, Δ indicates a control timing at which the determination result in Step Sa11 becomes "Yes" in the above-mentioned flowchart.

First, the subject user E starts the sound generator device 20 at a time t0 and lies down on his/her back on the bed 5. The subject user E is in an active state at first, and hence the estimation unit 230 estimates that the mind and body state of the subject user E is "excitation" (the determination result in Step Sa14 is "Yes"). Therefore, the control mode is set to "relaxation (Step Sa15). The mind and body state of the subject user E is shifted from "excitation" to "wakefulness" that is a relaxed state by the binaural beats of which frequency difference changes in a range of 7 Hz to 14 Hz and music reproduced at a tempo slightly lower than the heart rate detected in the subject user E, as well as the hypersonic effects. Specifically, the biological state (solid line) such as the heart rate and breathing, which is a movement average of sensor output, gradually approaches a target value (broken line) lower than the biological state.

At a time t1, the estimation unit 230 estimates that the mind and body state is "wakefulness" (the determination result in Step Sa16 is "Yes"). Therefore, the control mode is set to "sleep onset" (Step Sa18), and hence the subject user E falls asleep by the natural sound reproduced at a tempo further lower than the detected heart rate together with the hypersonic effects and the binaural beats of which frequency difference changes in one lower stage of 4 Hz to 7 Hz. At this time, the biological state continuously decreases while gradually approaching the target value.

At a time t2, the estimation unit 230 estimates that the mind and body state is "light sleep" (the determination result in Step Sa19 is "Yes"). Therefore, the control mode is set to "good sleep" (Step Sa20), and hence, the subject user E falls into deep sleep by the hypersonic effects and the natural sound reproduced at a lower tempo. At this time, the biological state has almost approached the lowest target value.

Due to the setting in accordance with "good sleep" of the control mode, it is estimated that the mind and body state is eventually "deep sleep" at a time t3 (the determination result in Step Sa21 is "Yes"). Therefore, the control mode is set to "ambient" (Step Sa22), and hence only the hypersonic effects are given.

It is known that a human repeats non-REM sleep and REM sleep alternately in a period of about 1 to 2 hours during sleep. Therefore, the non-REM sleep is not continued by the hypersonic effects, and hence the subject user E is shifted eventually to REM sleep. Therefore, the biological state tends to increase.

When it is estimated that the mind and body state is "REM sleep" at a time t4 before the wake-up time (the determination result in Step Sa23 is "Yes"), the control mode is set to "sleep onset" again. (Step Sa18). Therefore, the biological state of the subject user E decreases again to the target value due to the hypersonic effects, the binaural beats, and the natural sound reproduced at a tempo which is further lower than the heart rate.

Thus, the subject user E repeats non-REM sleep and REM sleep alternately. On the other hand, the sound generator device 20 guides the subject user E so that the sleep becomes deep by reproducing hypersonic and a natural sound in the case of "light sleep" of the non-REM sleep. In the case of "deep sleep", the sound generator device 20 attempts to relax the subject user E so that the sleep continues by the hypersonic. In the case of REM sleep, the sound generator device 20 guides the subject user E to sleep again by reproducing hypersonic, binaural beats, and a natural sound.

Note that, the repetition of non-REM sleep and REM sleep is omitted in FIG. 13.

On the other hand, when the wake-up time has come while the subject user E is "REM sleep" (the determination result in Step Sa24 becomes "Yes"), music is reproduced with a relatively large volume at a tempo twice a tempo of the heartbeat and in double time. Thus, this can awaken the subject user E refreshingly.

Note than, when the subject user E wakes up, it is estimated that the mind and body state is "wakefulness" at a time t5 (the determination result in Step Sa16 is "Yes", and the determination result in Step Sa17 is "No"). Therefore, the control mode is set to "MUTE" (Step Sa26), and hence a reproduced sound is suspended.

According to this embodiment, in order to improve sleep, a natural sound from the sound generator unit 430 and music from the sound generator unit 440 are reproduced at a tempo in accordance with the heart rate which is biological information. Therefore, the subject user E falls asleep while the mind and body state thereof is being shifted to the relaxed state. Of those, regarding the natural sound, the reading section of the waveform data is set at random from the waveform memory 431, and hence the subject user E can be prevented from being supplied with a boring feeling or an annoying feeling while the storage capacity required for the waveform memory 431 is suppressed.

Further, when the control mode is set to "relaxation", "sleep onset", and "good sleep", a plurality of the sound generator units 410, 420, 430, 440 are activated, and outputs from the activated sound generator units are mixed. Therefore, the effects such as preventing a boring sound or an annoying sound from being given to the subject user E can be obtained compared with a case in which the subject user E simply listens to only music or the like.

The sound generator unit 410 can adopt existing sound recordings, and further can impart the healing effects by hypersonic to the subject user E while suppressing the storage capacity of the waveform memory 411.

The present invention is not limited to the above-mentioned embodiment and can be applied and modified variously, for example, as described below. Further, any one selected from the following applications and modifications can be used or the following applications and modifications can also be combined appropriately.

In the above embodiment, the object to be set by the setting unit 220 is "improvement of sleep". However, other objects may be used. For example, the object may be "prevention of drowsiness", "relaxation", or the like. When the object is "prevention of drowsiness", the estimated mind and body state may be guided in an opposite direction to that of "improvement of sleep", and when the object is "relaxation", the estimated mind and body state in the above-mentioned embodiment may be limited to "excitation" and "wakefulness".

In the above embodiment, the brain wave, pulse wave (heartbeat), and body motion (breathing) of the subject user E are detected as biological information by the sensors 11, 12, 13. However, the mind and body state may be estimated by detecting the body temperature, blood pressure, and the like in addition to the above-mentioned biological information. Further, the mind and body state of the subject user E may be estimated by detecting the peripheral environment such as the temperature, humidity, and noise in addition to the biological information on the subject user E and considering them as a whole. The degree of fluctuation to be given to an output by each sound generator unit may be determined depending on the biological information such as heartbeat and breathing.

Further, in the above embodiment, the sleep state (mind and body state) is estimated by detecting the biological information on the subject user E by the sensors 11, 12, 13, and the sound generator units 410, 420, 430, 440 are controlled in accordance with the estimated sleep state. However, the following configuration may also be adopted.

For example, in advance, the sleep state is estimated by detecting the brain wave, pulse wave, breathing, and the like of the subject user E during sleep, and the brain wave, pulse wave, breathing, and the like of the subject user E are also concurrently detected by a simple sensor (for example, an acceleration sensor for detecting a body motion). Then, the sleep state and the detection result of the simple sensor are associated with each other and stored. Then, in the case of performing "improvement, of sleep" actually, only the simple sensor is attached to the subject user E, and the sleep state is estimated from the association of the stored sleep state based on the detection result obtained by the detection of the simple sensor. Thus, the sound generator units 410, 420, 430, 440 may be controlled in accordance with the estimated sleep state. In this case, an average of the detection results of a great number of subject users may be used, instead of the result of the subject user E, for associating the sleep state with the detection result of the simple sensor.

What is claimed is:

1. A sound generator device, comprising:
   an acquisition unit configured to acquire biological information including a breathing or a heart rate on a subject user;
   a sound generator configured to output a sound signal with a tempo corresponding to the biological information acquired by the acquisition unit,
   an estimation unit configured to estimate, based on the biological information acquired by the acquisition unit, a mind and body state including wakefulness, light sleep, and deep sleep of the subject user; and
   a sound generator control unit configured to change the mind and body state of the subject user by controlling a change amount of the tempo to be up or down according to the mind and body state estimated by the estimation unit, and
   wherein the sound generator includes a first sound generator unit and a second sound generator unit,
   wherein the first sound generator unit outputs a first sound signal at the tempo corresponding to the biological information acquired by the acquisition unit,
   wherein the second sound generator unit outputs a second sound signal different from the first sound signal at the tempo corresponding to the biological information acquired by the acquisition unit, and
   wherein the sound generator control unit configured to controls an output of the first sound signal of the first sound generator unit and an output of the second sound signal of the second sound generator unit corresponding to the mind and body state estimated by the estimation unit.

2. The sound generator device according to claim 1,
   wherein the tempo is lower than the heart rate of the subject user when the estimation unit estimate that the mind and body state of the subject user is wakefulness,
   wherein the tempo is lower than the heart rate of the subject user when the estimation unit estimate that the mind and body state of the subject user is light sleep, and
   wherein a degree of decrease in tempo with respect to the heart rate is different between the wakefulness state and the light sleep state.

3. The sound generator device according to claim 1,
   wherein the sound generator control unit configured to selects a control pattern based on the mind and body state estimated by the estimation unit among a plurality of the control patterns stored in advance, and controls the sound generator based on the selected control patterns.

4. A sound generator device, comprising:
   an acquisition unit configured to acquire biological information including a breathing or a heart rate on a subject user;
   a sound generator configured to output a sound signal with a tempo corresponding to the biological information acquired by the acquisition unit,
   an estimation unit configured to estimate, based on the biological information acquired by the acquisition unit, a mind and body state including wakefulness, light sleep, and deep sleep of the subject user; and
   a sound generator control unit configured to change the mind and body state of the subject user by controlling a change amount of the tempo to be up or down according to the mind and body state estimated by the estimation unit, and
   wherein the sound generator includes a first sound generator unit and a second sound generator unit,
   wherein the first sound generator unit outputs a first sound signal at the tempo corresponding to the biological information acquired by the acquisition unit,
   wherein the second sound generator unit outputs a second sound signal different from the first sound signal at the tempo corresponding to the biological information acquired by the acquisition unit,
   wherein the sound generator control unit configured to controls the tempo or an amplitude of the first sound signal or the second sound signal corresponding to the mind and body state estimated by the estimation unit, and
   wherein the sound generator control unit configured to gives fluctuation to the tempo or the amplitude of the first sound signal or the second sound signal.

5. The sound generator device according to claim 4,
   wherein the tempo is lower than the heart rate of the subject user when the estimation unit estimate that the mind and body state of the subject user is wakefulness,
   wherein the tempo is lower than the heart rate of the subject user when the estimation unit estimate that the mind and body state of the subject user is light sleep, and
   wherein a degree of decrease in tempo with respect to the heart rate is different between the wakefulness state and the light sleep state.

6. The sound generator device according to claim 4,
   wherein the sound generator control unit configured to selects a control pattern based on the mind and body state estimated by the estimation unit among a plurality of the control patterns stored in advance, and controls the sound generator based on the selected control patterns.

* * * * *